(12) United States Patent
Yan et al.

(10) Patent No.: US 11,911,396 B2
(45) Date of Patent: Feb. 27, 2024

(54) USE OF COMPOUND IN PREPARATION OF DRUG FOR TREATING CEREBRAL SMALL VESSEL DISEASE

(71) Applicant: GUANGZHOU CELLPROTEK PHARMACEUTICAL CO., LTD, Guangdong (CN)

(72) Inventors: Guangmei Yan, Guangdong (CN); Wei Yin, Guangdong (CN); Longxiang Sheng, Guangdong (CN); Bingzheng Lu, Guangdong (CN); Yijun Huang, Guangdong (CN); Suizhen Lin, Guangdong (CN)

(73) Assignee: GUANGZHOU CELLPROTEK PHARMACEUTICAL CO., LTD, Guangzhou (CN)

( * ) Notice: Subject to any disclaimer, the term of this patent is extended or adjusted under 35 U.S.C. 154(b) by 62 days.

(21) Appl. No.: 16/958,600

(22) PCT Filed: Dec. 28, 2018

(86) PCT No.: PCT/CN2018/124705
§ 371 (c)(1),
(2) Date: Jun. 26, 2020

(87) PCT Pub. No.: WO2019/129179
PCT Pub. Date: Jul. 4, 2019

(65) Prior Publication Data
US 2020/0330483 A1   Oct. 22, 2020

(30) Foreign Application Priority Data
Dec. 29, 2017   (CN) .......................... 201711484028.7

(51) Int. Cl.
| | | |
|---|---|---|
| A61K 38/36 | (2006.01) |
| A61K 31/568 | (2006.01) |
| A61P 7/04 | (2006.01) |
| A61P 9/10 | (2006.01) |
| A61P 9/14 | (2006.01) |

(52) U.S. Cl.
CPC .............. *A61K 31/568* (2013.01); *A61P 9/14* (2018.01)

(58) Field of Classification Search
CPC .. A61P 25/28; A61P 25/00; A61P 9/10; A61P 43/00; A61P 7/04; A61K 9/0085; A61K 31/568; A61K 31/5685; A61K 38/36; A61B 5/055; C07D 401/14; C07D 413/14
See application file for complete search history.

(56) References Cited

U.S. PATENT DOCUMENTS

| 2013/0157993 A1 | 6/2013 | Yan et al. |
| 2017/0042909 A1 | 2/2017 | Yin et al. |
| 2017/0049744 A1* | 2/2017 | Yanamoto ................. A61P 9/00 |

FOREIGN PATENT DOCUMENTS

| CA | 2946647 C | * 10/2018 | ............... A61P 7/10 |
| CN | 101683348 A | 3/2010 | |
| CN | 101884638 A | 11/2010 | |
| CN | 105012313 A | 11/2015 | |

OTHER PUBLICATIONS

Fan et al. Reversible Brain Abnormalities in People Without Signs of Mountain Sickness During High-Altitude Exposure. Sep. 16, 2016. www.nature.com/scentificreports. (Year: 2016).*
Vernooij et al. Use of Antithrombotic Drugs and the Presence of Cerebral Microbleeds. Jun. 2009. Arch Neurol. vol. 66. No. 6. (Year: 2009).*
Wahl et al. Relationship between radiation dose and microbleed formation in patients with malignant glioma. Aug. 10, 2017. Radiation Oncology. vol. 12. Issue 126. (Year: 2017).*
Noorbakhsh-Sabet et al. Uncommon Causes of Cerebral Microbleeds. Aug. 18, 2017. Journal of Stroke and Cerebrovascular Diseases. vol. 26. Issue 10. pp. 2043-2049. (Year: 2017).*
English Translation of the International Search Report issued in PCT Application No. PCT/CN2018/124705 dated Apr. 8, 2019, 2 pages.
Yan et al., "Neuroprotectant androst-3β, 5α, 6β-triol suppresses TNF-α-induced endothelial adhesion molecules expression and neutrophil adhesion to endothelial cells by attenuation of CYLD-NF-kB pathway", Biochemical and Biophysical Research Communication, 483 (2017) pp. 892-896.
International Search Report and Written Opinion issued in PCT Application No. PCT/CN2018/124705 dated Apr. 8, 2019, 7 pages.
Du X., "Comprehensive Diagnosis and Treatment for CSVD and Rehabilitation Guidance", Publisher Tianjin Science and Technology Publishing House, Jun. 2013, 3 pages.
English Translation of the Relevant Part of Du X., "Comprehensive Diagnosis and Treatment for CSVD and Rehabilitation Guidance", Publisher Tianjin Science and Technology Publishing House, Jun. 2013, 2 pages.
Bath et al., "Pharmacological treatment and prevention of cerebral small vessel disease: a review of potential interventions", International Journal of Stroke, 2015, vol. 10, pp. 469-478 (10 pages).
Charidimou et al., "Cerebral microbleeds: A guide to detection and clinical relevance in different disease settings", Neuroradiology, 2013 (58 pages).

(Continued)

*Primary Examiner* — Tracy Liu
(74) *Attorney, Agent, or Firm* — Foley & Lardner LLP

(57) ABSTRACT

Disclosed is use of 5α-androst-3β,5,6β-triol or an analogue, a deuterated compound or a pharmaceutically acceptable salt thereof in the manufacture of a medicament for the treatment of cerebral small vessel disease in a patient. The cerebral small vessel disease is preferably cerebral microbleed. The cerebral microbleed is spontaneous cerebral microbleed, drug-related cerebral microbleed, or traumatic cerebral microbleed. The present invention demonstrates that these compounds significantly enhance the clearance of extravascular hemoglobin, and thus can be used to treat cerebral small vessel disease.

14 Claims, 7 Drawing Sheets

(56) References Cited

OTHER PUBLICATIONS

Haussen et al., "Statin Use and Mircorbleeds in Patients with Spontaneous Intracerebral Hemorrhage", Stroke, 2012, vol. 43, pp. 2677-2681 (5 pages).
Khalilzada et al., "Sublingual Microvascular Changes in Patients With Cerebral Small Vessel Disease", Stroke, 2011, vol. 42, pp. 2071-2073 (3 pages).
Shi et al., "Update on cerebral small vessel disease: a dynamic whole-brain disease", Stroke and Vascular Neurology, 2016, vol. 1, pp. 83-92 (10 pages).
Thomas Gregor Isaac et al., "Cerebral Small Vessel Disease Clinical, Neuropsychological, and Radiological Phenotypes, Histopathological Correlates, and Described Genotypes: A Review", Journal of Geriatrics, 2015 (13 pages).
Wardlaw et al., "Mechanisms underlying sporadic cerebral small vessel disease: insights or neuroimaging", Lancet Neurol, 2013, vol. 12, No. 5, pp. 1-26 (27 pages).
Kallenberg, Kai, et al.; "Microhemorrhages in nonfatal high-altitude cerebral edema"; Journal of Cerebral Blood Flow & Metabolism, vol. 28; Jun. 4, 2008; pp. 1635-1642.
Oyama, Yutaka, et al.; "Astrocyte as a target cell for cerebral edema therapeutic drug' The role of astroglia in increasing vascular permeability during brain injury"; Journal of Japanese Pharmacology, vol. 144, No. 3; Sep. 10, 2014; 7 pages.
Pantoni, Leonardo; "Cerebral small vessel disease: from pathogenesis and clinical characteristics to therapeutic challenges"; The Lancet Neurology, vol. 9, issue 7; Jun. 16, 2010; pp. 689-701.
Hu et al.; "Association Between Cerebral Microbleeds and Enlarged Perivascular Spaces"; Med J Qilu, vol. 32, No. 2; Apr. 2017; 4 pages.
Teng et al.; "Enlarged perivascular spaces and cognitive impairment"; Int J Cerebrovasc Dis, vol. 27, No. 2; Feb. 2019; 5 pages.

\* cited by examiner

A.

B.

A.

B.

A.

B.

A.

B.

A.

B.

C.

A.

B.

C.

D

E

F.

G.

Fig. 6 (con.)

USE OF COMPOUND IN PREPARATION OF DRUG FOR TREATING CEREBRAL SMALL VESSEL DISEASE

CROSS-REFERENCE TO RELATED APPLICATIONS

This application is a national stage entry under 35 U.S.C. § 371 of International Patent Application No. PCT/CN2018/124705 filed Dec. 28, 2018, which in turn claims priority to Chinese Application No. 201711484028.7, filed Dec. 29, 2017, the entire content of each of which are hereby incorporated by reference.

TECHNICAL FIELD

The present invention relates to new pharmaceutical uses of 5α-androst-3β,5,6β-triol ("triol") and its analogues, in particular to uses of these compounds in the treatment of cerebral small vessel disease.

BACKGROUND

Cerebral small vessels refer to small perforating arteries and small arteries (diameter 40~200 μm), capillaries, and small veins in the brain, which constitute the basic unit of blood supply to brain tissue and play an important role in maintaining brain function[1]. The large and small vessels in the brain together constitute the vascular tree. They are structurally continuous, jointly affected by hemodynamics, and jointly exposed to risk factors. Therefore, the pathological changes of large and small vessels in the brain should theoretically have a parallel correlation in terms of severity. However, in clinical practice, an inconsistency is often found between these two kinds of vessels. For example, patients with severe cerebral small vessel disease but not complicated with large cerebral artery stenosis are often found, and vice versa[2].

Cerebral small vessel disease (CSVD) refers to syndromes of clinical, cognitive, imaging and pathological manifestations caused by various lesions of the small vessels[3]. Traditionally, it refers to the clinical and imaging manifestations caused by small perforating artery and small artery lesions. CSVD mainly clinically manifests as stroke (deep small infarction, cerebral hemorrhage), cognitive and emotional disorders, and overall functional decline. In imaging, it manifests as lacunar infarction (LI), lacuna, white matter lesions (WML), enlarged perivascular space (EPVS) and cerebral microbleeds (CMB), etc[1].

The specific pathogenesis of CSVD is related to vascular endothelial dysfunction, blood-brain barrier (BBB) damage, inflammatory mechanisms, genetic factors, and ischemic hypoperfusion injury, of which BBB damage is the core mechanism. BBB damage and destruction leads to increased permeability, which allows blood components extravasate to the surrounding tissues and brain parenchyma, causing corresponding pathophysiological changes, resulting in CSVD-related imaging and pathological changes[4].

Cerebral microbleed is one of the manifestations of cerebral small vessel disease, and is a subclinical damage to the brain parenchyma caused by microvascular disease in the brain. It is characterized by a small amount of blood leakage, and red blood cells overflowing the vessels generate hemosiderin images. Depending on the age of the lesion, fresh red blood cells, deposited hemosiderin granules, or hemosiderin-engulfing macrophages can be seen around the vessels.

CMB manifests as lesions with small signal loss on T2* weighted sequences (or other sequences sensitive to susceptibility), with halos around the lesions. The lesions generally have a diameter of 2 to 5 mm, up to 10 mm[5]. These lesions on MR images are called "signal void", "susceptibility artifact", "black hole", "dot", "microbleed", "old microbleed (OMB)", "multifocal signal loss lesion", or "microhemorrhage (MH)". It is usually distributed in the junction of the cortex and the subcortex, the gray matter nucleus in the deep cortex, the white matter of the cerebral hemisphere, the brain stem, and the cerebellum. Magnetic sensitivity weighted imaging (SWI) sequence is more sensitive to CMBs than T2*W-GRE sequence.

CMBs are mostly considered asymptomatic and lack acute clinical manifestations. Studies have shown that cerebral microbleeds have a certain relationship with age, cardiovascular risk factors, white matter degeneration, stroke, and post-stroke affective disorders. In addition, cerebral microbleed is also an important pathological cause of brain injury in acute and chronic high-altitude diseases[6]. Cerebral microbleed was found in brain tissue[7] or retina[8] in MRI imaging examination of autopsy of patients with high altitude disease or survivors of high-altitude cerebral edema. Using MRI susceptibility weighted imaging (SWI) to examine cerebral microbleeds in patients with chronic mountain sickness (CMS), it was found that 11 of 20 (55%) confirmed CMS patients had cerebral microbleeds, and the positive rate of cerebral microbleeds detected in the CMS group was significantly higher than that in the normal population[9].

The widespread use of thrombolytic drugs (such as tissue plasminogen activator (t-PA), streptokinase (SK)), anticoagulant drugs (such as warfarin), and antiplatelet drugs (such as aspirin) in the antithrombotic therapy has led to a significant increase in the incidence of drug-related primary intracerebral hemorrhage (ICH). Studies have shown that comparing patients with warfarin-related ICH and patients with spontaneous ICH, CMB is more common in the former. Current research suggests that CMB is associated with an increased risk of bleeding associated with anticoagulant drugs. The risk of aspirin-related ICH increases significantly with the number of CMB lesions. A meta-analysis showed that comparing aspirin users with non-aspirin users, CMB and ICH were related (OR=1.7). Another study showed that patients with stroke who used high-dose statins (such as atorvastatin) had a slightly increased incidence of ICH. The incidence of brain lobe CMB in statin users is about twice that of non-statin users, but no significant difference was found in other parts, suggesting that statins may increase the risk of bleeding in patients with cerebral amyloid angiopathy.

Surgery can also cause damage to the central nervous system, including direct damage to the nerve tissue by a surgery in the central nervous system (including the brain and the notochord) and histopathological changes in the nervous system caused by changes in blood supply and bleeding during a surgery, including tissue edema, bleeding, microbleeds, infarction, and microinfarction. Common surgeries that cause damage to the central nervous system include, but are not limited to, cerebral aneurysm clipping or embolization, brain tumor resection, and other surgeries that directly involve the central nervous system.

However, at present, there is still a lack of effective drugs for the treatment of cerebral microbleeds. It is of great clinical significance to provide a medicine that relieves or clears cerebral microbleeds.

SUMMARY

The present invention is based on the inventors' discovery that the compounds of formula I improve the clearance of free hemoglobin in brain tissue, and provides new use of the compounds of formula I:

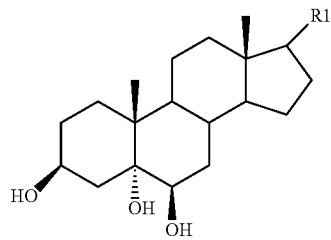

in the treatment of cerebral small vessel disease, wherein $R_1$ is H, an alkyl or terminal alkenyl having 1 to 5 carbon atoms, or —$CH(CH_3)(CH_2)_3CH(CH_3)_2$.

Accordingly, an aspect of the present invention provides use of a compound of formula I:

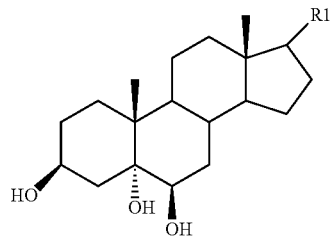

or a deuterated compound or a pharmaceutically acceptable salt thereof in the manufacture of a medicament for the treatment of cerebral small vessel disease, wherein $R_1$ is H, an alkyl or terminal alkenyl having 1 to 5 carbon atoms, or —$CH(CH_3)(CH_2)_3CH(CH_3)_2$.

In one embodiment, $R_1$ is preferably H, and the compound is 5α-androst-3β,5,6β-triol (sometimes abbreviated as "Triol" hereinafter). In one embodiment, $R_1$ is selected from a group consisting of =$CHCH_2CH_3$, —$CH(CH_3)_2$, —$CH(CH_2)_3CH_3$ and —$CH(CH_3)(CH_2)_3CH(CH_3)_2$.

In some embodiments, the cerebral small vessel disease is preferably cerebral microbleed. In some embodiments, the cerebral microbleed is spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

Another aspect of the present invention provides a method for treating cerebral microbleed in a patient, the method comprising administering to the patient an effective amount of a compound of formula I:

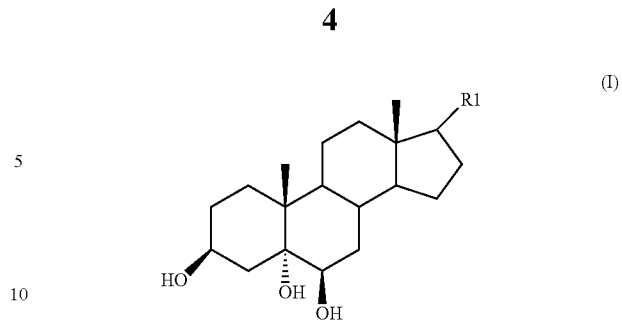

or a deuterated compound or a pharmaceutically acceptable salt thereof, or a pharmaceutical composition comprising the compound of formula I or a deuterated compound or a pharmaceutically acceptable salt thereof, wherein $R_1$ is H, an alkyl or terminal alkenyl having 1 to 5 carbon atoms, or —$CH(CH_3)(CH_2)_3CH(CH_3)_2$.

In one embodiment, $R_1$ is preferably H. In one embodiment, $R_1$ is selected from a group consisting of =$CHCH_2CH_3$, —$CH(CH_3)_2$, —$CH(CH_2)_3CH_3$ and —$CH(CH_3)(CH_2)_3CH(CH_3)_2$.

In some embodiments, the cerebral microbleed in the patient is confirmed by MRI. In some embodiments, the patient is suffering from spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

A further aspect of the present invention provides a compound of formula I:

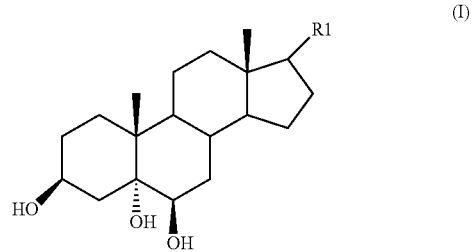

or a deuterated compound or a pharmaceutically acceptable salt thereof for use in the treatment of cerebral microbleed in a patient, wherein $R_1$ is H, an alkyl or terminal alkenyl having 1 to 5 carbon atoms, or —$CH(CH_3)(CH_2)_3CH(CH_3)_2$.

In one embodiment, $R_1$ is preferably H. In one embodiment, $R_1$ is selected from a group consisting of =$CHCH_2CH_3$, —$CH(CH_3)_2$, —$CH(CH_2)_3CH_3$ and —$CH(CH_3)(CH_2)_3CH(CH_3)_2$.

In some embodiments, the cerebral microbleed in the patient is confirmed by MRI. In some embodiments, the patient is suffering from spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

Another aspect of the present invention provides a method for enhancing the clearance of free hemoglobin outside the cerebral vessels in a patient, the method comprising administering to the patient an effective amount of a compound of formula I:

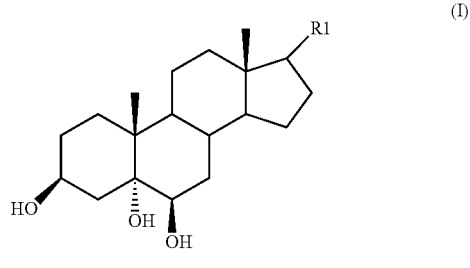
(I)

or a deuterated compound or a pharmaceutically acceptable salt thereof, or a pharmaceutical composition comprising the compound of formula I or a deuterated compound or a pharmaceutically acceptable salt thereof, wherein $R_1$ is H, an alkyl or terminal alkenyl having 1 to 5 carbon atoms, or —CH(CH$_3$)(CH$_2$)$_3$CH(CH$_3$)$_2$.

In one embodiment, $R_1$ is preferably H. In one embodiment, $R_1$ is selected from a group consisting of =CHCH$_2$CH$_3$, —CH(CH$_3$)$_2$, —CH(CH$_2$)$_3$CH$_3$ and —CH(CH$_3$)(CH$_2$)$_3$CH(CH$_3$)$_2$.

A further aspect of the present invention provides a method for clearing free hemoglobin outside the cerebral vessels in a patient, the method comprising administering to the patient an effective amount of a compound of formula I:

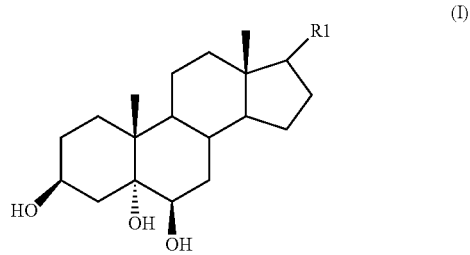
(I)

or a deuterated compound or a pharmaceutically acceptable salt thereof, or a pharmaceutical composition comprising the compound of formula I or a deuterated compound or a pharmaceutically acceptable salt thereof, wherein $R_1$ is H, an alkyl or terminal alkenyl having 1 to 5 carbon atoms, or —CH(CH$_3$)(CH$_2$)$_3$CH(CH$_3$)$_2$.

In one embodiment, $R_1$ is preferably H. In one embodiment, $R_1$ is selected from a group consisting of =CHCH$_2$CH$_3$, —CH(CH$_3$)$_2$, —CH(CH$_2$)$_3$CH$_3$ and —CH(CH$_3$)(CH$_2$)$_3$CH(CH$_3$)$_2$.

The free hemoglobin is caused by spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

A further aspect of the present invention provides a method for treating cerebral small vessel disease in a patient, the method comprising administering to the patient a therapeutically effective amount of a compound of formula I:

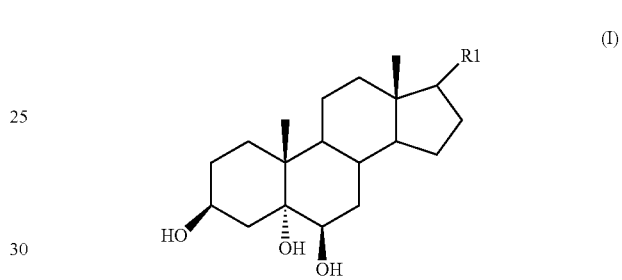
(I)

or a deuterated compound or a pharmaceutically acceptable salt thereof, or administering a therapeutically effective amount of a pharmaceutical composition comprising the compound of formula I or a deuterated compound or a pharmaceutically acceptable salt thereof, wherein $R_1$ is H, an alkyl or terminal alkenyl having 1 to 5 carbon atoms, or —CH(CH$_3$)(CH$_2$)$_3$CH(CH$_3$)$_2$.

In one embodiment, $R_1$ is preferably H. In one embodiment, $R_1$ is selected from a group consisting of =CHCH$_2$CH$_3$, —CH(CH$_3$)$_2$, —CH(CH$_2$)$_3$CH$_3$ and —CH(CH$_3$)(CH$_2$)$_3$CH(CH$_3$)$_2$.

In some embodiments, the cerebral small vessel disease is cerebral microbleed. In some embodiments, the cerebral microbleed in the patient is confirmed by MRI. In some embodiments, the patient is suffering from spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

DETAILED DESCRIPTION OF THE INVENTION

Figure 1:
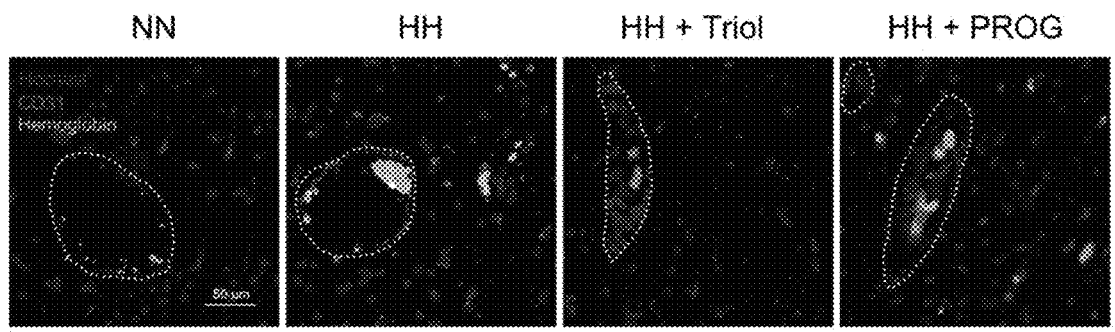
FIG. 1. Acute hypobaric hypoxia caused an increase in extravascular distribution of free hemoglobin in the brain tissue of the prefrontal cortex of cynomolgus monkeys (*Macaca fascicularis*). A. Immunofluorescence imaging of the brain tissue of cynomolgus monkeys, in which the vascular endothelial cell marker CD31 showed a red signal, indicating the position of the blood vessel, and the dotted line showed the outline of the vessel; free hemoglobin was shown in green; and the nucleus was shown in blue. B. MFI (Mean Fluorescence Intensity) was quantified using Nikon NIS-Element software. The statistics of the relative fluorescence intensity of free hemoglobin distributed extravascularly in the brain tissue of cynomolgus monkeys was shown, and one-way ANOVA analysis and Dunnutt's t test were used to perform statistical tests, **, $p<0.01$, ns, no statistical difference, n=4. NN: Normobaric Normoxia group; HH: Hypobaric Hypoxia group; HH+Triol: Hypobaric Hypoxia with Triol administration group; HH+PROG: Hypobaric Hypoxia with control drug administration group. PROG represents the control drug progesterone.
Figure 1:
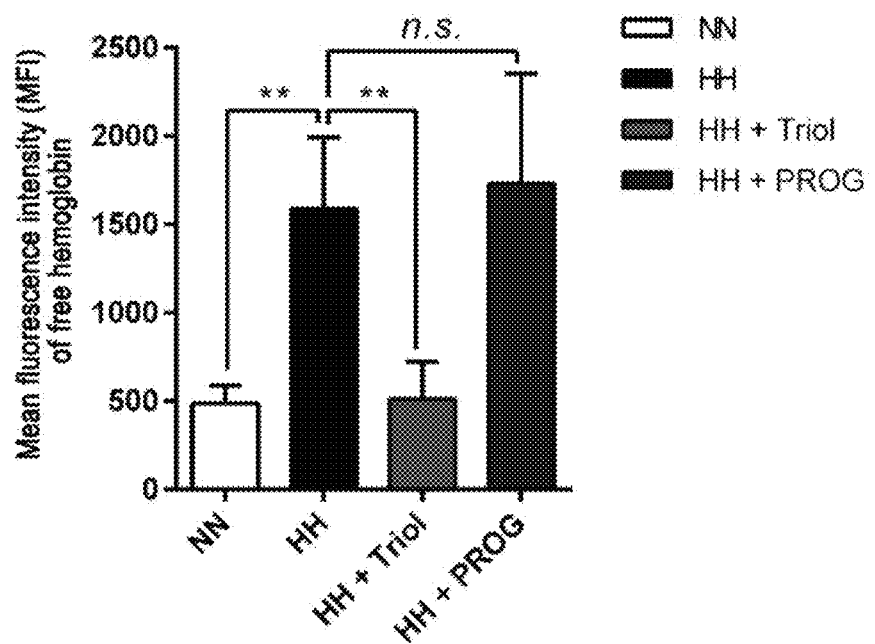

As used herein, the term "composition" refers to a formulation suitable for administration to an intended animal subject for therapeutic purposes, which comprises at least one pharmaceutically active component, such as a compound. Optionally, the composition further comprises at least one pharmaceutically acceptable carrier or excipient.

The term "pharmaceutically acceptable" means that the substance does not have the property that, considering the disease or condition to be treated and the respective route of administration, will allow rational and prudent medical practitioners to avoid administering the substance to the patient. For example, for injectables, it is often required that such substance is substantially sterile.

As used herein, the terms "therapeutically effective amount" and "effective amount" mean that the substance and the amount of the substance are effective to prevent, alleviate or ameliorate one or more symptoms of a disease or condition, and/or prolong the survival of the subject receiving the treatment.

The term "cerebral small vessel disease" or "CSVD" refers to the syndrome of clinical, cognitive, imaging and pathological manifestations caused by various lesions of small perforating arteries and small arteries (diameter 40~200 μm), capillaries and small veins in the brain. In a preferred embodiment, "cerebral small vessel disease" manifests as an impaired blood-brain barrier, and the destruction of the blood-brain barrier leads to increased permeability, which allows blood components extravasate to the surrounding tissues and brain parenchyma, causing corresponding pathophysiological changes, resulting in CSVD-related imaging and pathological changes. In a specific embodiment, the "cerebral small vessel disease" does not include hemorrhagic stroke.

The term "cerebral microbleed" refers to bleeding within a region of the brain that is less than about 1 cm in diameter. Cerebral microbleeds can be detected by brain MRI (including T2*weighted GRE MRI), and can be a "asymptomatic cerebral microbleed" that shows no symptoms, or may be associated with symptoms such as transient or permanent focal motor or sensory disturbances, ataxia, aphasia, dysarthria (namely "symptomatic cerebral microbleed"[10]). In some embodiments, cerebral microbleed manifests as a significantly increased distribution of extravascular free hemoglobin.

The term "spontaneous cerebral microbleed" herein refers to intracerebral bleeding caused by spontaneous rupture of cerebral vessels (usually veins or capillaries) caused by various causes under non-traumatic conditions. Spontaneous cerebral bleed is a multifactorial disease, which is affected by environmental and genetic factors. For example, advanced age is closely related to spontaneous cerebral microbleed (age-related cerebral microbleed). Spontaneous cerebral microbleed caused by a disease includes those caused by hypertension (such as long-term hypertension), ischemic stroke and hemorrhagic stroke, which are accordingly referred to herein as "hypertensive cerebral microbleed", "cerebral microbleed associated with ischemic stroke" and "cerebral microbleed associated with hemorrhagic stroke". Other environmental factors or disease factors may also cause cerebral microbleed, and the present invention is expected to be applicable to the treatment of these cerebral microbleeds not specifically listed.

The term "drug-related cerebral microbleed" refers herein to cerebral microbleeds caused by drugs. These drugs may include, but are not limited to, thrombolytic drugs, anticoagulant drugs, antiplatelet agglutination drugs, or statin drugs.

With the widespread use of thrombolytic therapy, thrombolytic drugs have also developed from the first generation to the third generation. Early first-generation thrombolytic drugs are streptokinase (SK), urokinase (UK), lumbrokinase, pro-urokinase, staphylokinase, methoxybenzoyl plasminogen streptokinase activator, and snake venom antithrombotic enzyme. The second-generation thrombolytic drug "alteplase" is a recombinant tissue-type plasminogen activator (t-PA), which is the world's first genetic recombinant thrombolytic drug, developed and marketed by Genetech in the U.S. At present, the thrombolytic drugs have developed to the third generation. "Reteplase" developed by Boehringer Mannheim GmbH in Germany in 1996 is a representative. Reteplase is a protein-modified drug. It is a deletion mutation of recombinant human tissue-type fibrinolytic activator, and has the advantages of long half-life, strong thrombolytic effect, and small side effects. The third-generation thrombolytic drugs under research and development are all t-PA variants, such as TNKase (teneplase, TNK-t-PA), Monteplase, La noteplase (nateplase, n-PA), etc. The common characteristics of the third generation thrombolytic drugs are capabilities of rapid thrombolysis, opening clogged coronary arteries, and restoring blood circulation, with a cure rate of 73% to 83%.

Anticoagulant drugs, also known as anticoagulants, are used to prevent and treat diseases of intravascular embolism or thrombosis, and prevent stroke or other thrombotic diseases. The most frequently used anticoagulants in clinical use include: parenteral anticoagulants (such as heparin, enoxaparin, tiatarparin, adiheparin), coumarin anticoagulants (such as warfarin, dicoumarin, coumarin nitrate), in vitro anticoagulants (such as sodium citrate), thrombin inhibitors (such as hirudin, argatroban).

Antiplatelet agglutination drugs can be divided into four categories according to the action site and route of the drug: (1) cyclooxygenase inhibitors (thromboxane A2 inhibitors, salicylic acid): commonly used drugs are aspirin tablets. (2) Phosphodiesterase inhibitors: such as cilostazol (Pedar), dipyridamole (Pansentine), etc. Cilostazol (Pedar) inhibits the activity of platelet and vascular smooth muscle phosphodiesterase, increases the concentration of cAMP in platelets and smooth muscle, and more potently inhibits platelets than aspirin and ticlopidine (Ticlid), and has a dissociative effect on platelet aggregates and is the drug of choice for peripheral vascular disease. Clinically it is mainly used for the treatment of local diseases such as chronic arterial occlusive ulcers, pain and cold sensation. It is used for patients with intermittent claudication without cardiac insufficiency, and can improve symptoms and increase walking distance. Oral conventional dose of dipyridamole (Pansentine) can increase the incidence of exercise-induced myocardial infarction in patients with stable angina, so it is currently limited to patients with a history of stroke and no coronary heart disease. Dipyridamole is not recommended for patients with coronary heart disease. (3) ADP receptor antagonists (thiophene pyridines): such as clopidogrel (Plavix, Talcom), ticlopidine (Ticlid, Ticlop, etc.), etc. (4) Platelet glycoprotein II b/III antagonists (GP II b/IIIa receptor antagonists) such as monoclonal antibody abciximab, peptide inhibitor eptifibatide, and non-peptide inhibitor tirofiban and so on.

Statin drugs, also known as 3-hydroxy 3-methylglutaryl coenzyme A (HMG-CoA) reductase inhibitors, can significantly reduce cholesterol (TC), low density lipoprotein (LDL-C) and apoB (apolipoprotein), and at the same time reduce triglyceride (TG) and slightly increase high-density lipoprotein (HDL-C). It is suitable for primary hypercholesterolemia and mixed hyperlipidemia, and at the present is a very important drug for the prevention and treatment of hypercholesterolemia and atherosclerosis. The first-generation drugs currently on the market include lovastatin and simvastatin; the second-generation drugs include pravastatin and fluvastatin; the third-generation drugs include atorvastatin, rosuvastatin, and pitavastatin.

The term "traumatic cerebral microbleed" herein refers to intracerebral microbleed caused by trauma, such as intracerebral microbleed caused by surgery-induced trauma, mild traumatic brain injury (TBI) or chronic craniocerebral trauma. The term "surgery-derived cerebral microbleed" or "surgery-induced cerebral microbleed" refers to intracerebral microbleed caused by surgery. In some embodiments, the surgery refers to a surgery that directly involves the central nervous system. In some embodiments, the surgery refers to cerebral aneurysm clipping or embolization or brain tumor resection.

Compound of Formula I, or a Deuterated Compound or a Pharmaceutically Acceptable Salt Thereof Compounds that are applicable in the methods or uses of the present invention include the compound of formula I:

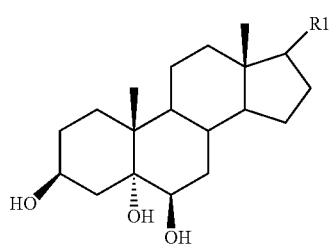

(I)

or a deuterated compound or a pharmaceutically acceptable salt thereof, wherein $R_1$ is H, an alkyl or terminal alkenyl having 1 to 5 carbon atoms, or —CH(CH$_3$)(CH$_2$)$_3$CH(CH$_3$)$_2$, which is also referred to herein as "the compound of the present invention". In one embodiment, $R_1$ is H, and the compound is 5α-androst-3β,5,6β-triol (sometimes abbreviated as "Triol" hereinafter), having the structure of formula II:

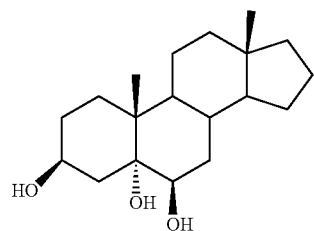

(II)

It has been confirmed that Triol is a neuron protective agent effective against acute ischemic hypoxic brain damage.

In one embodiment, $R_1$ is =CHCH$_2$CH$_3$, and the compound is 17-propylene-androst-3β,5α,6β-triol. In one embodiment, $R_1$ is —CH(CH$_3$)$_2$, and the compound is 17-isopropyl-androst-3α,5α,6β-triol. In one embodiment, $R_1$ is —CH(CH$_2$)$_3$CH$_3$, and the compound is 17-butylandrost-3α,5α,6β-triol. In one embodiment, $R_1$ is —CH(CH$_3$)(CH$_2$)$_3$CH(CH$_3$)$_2$, and the compound is cholestane-3α,5α,6β-triol.

The compounds of the present invention can be formulated in the form of pharmaceutically acceptable salts. The expected pharmaceutically acceptable salt forms include, but are not limited to, mono-, di-, tri-, and tetra-salts. Pharmaceutically acceptable salts are non-toxic at the amount and concentration to which they are administered. The preparation of such salts can facilitate pharmacological uses by changing the physical properties of the compound without preventing it from exerting physiological effects. Useful changes in physical properties include lowering the melting point to facilitate transmucosal administration, and increasing solubility to facilitate administration of higher concentrations of drugs.

Pharmaceutically acceptable salts include acid addition salts, such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate salts. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid and quinic acid.

When acidic functional groups such as carboxylic acids or phenols are present, pharmaceutically acceptable salts also include base addition salts, such as those containing benzathine penicillin, chloroprocaine, choline, diethanolamine, ethanolamine, tert-butylamine, ethylenediamine, meglumine, procaine, aluminum, calcium, lithium, magnesium, potassium, sodium, ammonium, alkylamine and zinc. Such salts can be prepared using appropriate corresponding bases.

Pharmaceutically acceptable salts can be prepared through standard techniques. For example, the compound in its free base form can be dissolved in a suitable solvent, such as an aqueous solution or a water-alcohol solution containing a suitable acid, and then the solution is evaporated for separation. In another example, the salt is prepared by reacting the free base with an acid in an organic solvent.

Thus, for example, if the specific compound is a base, the desired pharmaceutically acceptable salt can be prepared by any suitable method available in the art, for example, by treating the free base with an inorganic acid such as hydrochloric acid, hydrobromic acid, sulfuric acid, nitric acid, phosphoric, or the like, or an organic acid such as acetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid, α-hydroxy acid such as citric acid or tartaric acid, amino acid such as aspartic acid or glutamic acid, aromatic acid such as benzoic acid or cinnamic acid, sulfonic acid such as p-toluenesulfonic acid or ethanesulfonic acid or the like.

Similarly, if the specific compound is an acid, the desired pharmaceutically acceptable salt can be prepared by any suitable method, for example, by treating the free acid with an inorganic base or an organic base, such as an amine (primary, secondary or tertiary amine), alkali metal hydroxides or alkaline earth metal hydroxides or the like. Illustrative examples of suitable salts include organic salts derived from amino acids (such as L-glycine, L-lysine, and L-arginine), ammonia, primary, secondary, and tertiary amines, and cyclic amines (such as hydroxyethylpyrrolidine, piperidine, morpholine and piperazine), and inorganic salts derived from sodium, calcium, potassium, magnesium, manganese, iron, copper, zinc, aluminum and lithium.

The pharmaceutically acceptable salts of the compounds can exist as complexes. Examples of complexes include 8-chlorotheophylline complexes (such as, for example, diphenhydramate: diphenhydramine 8-chlorotheophylline (1:1) complex; Dramamine) and various complexes comprising cyclodextrin.

The present invention is also intended to include the use of pharmaceutically acceptable deuterated compounds or other non-radioactive substituted compounds. Deuteration is to replace one or more or all of the hydrogen in the active molecular group of the drug with isotope deuterium. Because it is non-toxic and non-radioactive, and it is about 6-9 times more stable than the carbon-hydrogen bond, it can close the metabolic site and prolong the half-life of the drug, thereby reducing the therapeutic dose without affecting the pharmacological activity of the drug, thus it is considered to be an excellent modification method.

Pharmaceutical Composition

Another aspect of the present invention provides a pharmaceutical composition comprising an effective amount of a compound of formula I, or a deuterated compound or a pharmaceutically acceptable salt thereof, and a pharmaceutically acceptable carrier.

In the present invention, "pharmaceutical composition" refers to a composition comprising a compound of formula I and a pharmaceutically acceptable carrier, wherein the compound and the pharmaceutically acceptable carrier are present in the composition in a mixed form. The composition will generally be used in the treatment of human subjects. However, they can also be used to treat similar or same conditions in other animal subjects. In this context, the terms "subject", "animal subject" and similar terms refer to human and non-human vertebrates, such as mammals, such as non-human primates, competitive animals and commercial animals, such as horses, cattle, pigs, sheep, rodents, and pets (such as dogs and cats).

The appropriate dosage form depends in part on the use or route of administration, for example, it can be oral, transdermal, transmucosal, by inhalation or by injection (parenteral). Such dosage forms should enable the compound to reach target cells. Other factors are well known in the art and include considerations such as toxicity and dosage forms that delay the compound or composition from exerting its effects.

Carriers or excipients can be used to produce the composition. The carriers or excipients can be selected to facilitate administration of the compound. Examples of carriers include calcium carbonate, calcium phosphate, various sugars (such as lactose, glucose, or sucrose), or starch types, cellulose derivatives, gelatin, vegetable oils, polyethylene glycol, and physiologically compatible solvents. Examples of physiologically compatible solvents include sterile water for injection (WFI) solutions, saline solutions, and glucose.

The composition or components of the composition can be administered by different routes, including intravenous, intraperitoneal, subcutaneous, intramuscular, oral, transmucosal, rectal, transdermal, or inhalation routes. In some embodiments, injections or lyophilized powder injections are preferred. For oral administration, for example, the compound may be formulated into conventional oral dosage forms such as capsules and tablets, and liquid preparations such as syrups, elixirs and concentrated drops.

Pharmaceutical preparations for oral use can be obtained, for example, by combining the composition or its components with solid excipients, optionally grinding the resulting mixture, and treating the mixture of particles after adding suitable adjuvants (if necessary), thereby obtaining tablets or dragees. Suitable excipients are, in particular, fillers such as sugars including lactose, sucrose, mannitol or sorbitol; cellulose preparations such as corn starch, wheat starch, rice starch, potato starch, gelatin, tragacanth, methyl cellulose, hydroxypropyl methyl cellulose, sodium carboxymethyl cellulose (CMC) and/or polyvinylpyrrolidone (PVP: povidone). If desired, disintegrating agents may be added, such as cross-linked polyvinylpyrrolidone, agar, or alginic acid or their salts, such as sodium alginate.

Alternatively, injections (parenteral administration) can be used, for example intramuscular, intravenous, intraperitoneal and/or subcutaneous injection. For injection, the composition of the invention or its components are formulated as a sterile liquid solution, preferably in a physiologically compatible buffer or solution, such as saline solution, Hank's solution or Ringer's solution. In addition, the composition or its components can be formulated in a solid form and re-dissolved or suspended immediately before use. It can also be produced in the form of lyophilized powder.

Administration can also be by transmucosal, topical or transdermal means. For transmucosal, topical or transdermal administration, penetrants suitable for the barrier to be penetrated are used in the formulation. Such penetrants are generally known in the art and include, for example, for transmucosal administration, bile salts and fusidic acid derivatives. In addition, detergents can be used to promote penetration. Transmucosal administration, for example, can be by nasal spray or suppository (via rectum or vagina).

The effective amount of various components to be administered can be determined by standard procedures, taking into account factors such as $IC_{50}$ of the compound, the biological half-life of the compound, the age, size, and body weight of the subject, and the conditions associated with the subject. The importance of these and other factors is well known to those of ordinary skill in the art. Generally, the dosage will be between about 0.01 mg/kg and 50 mg/kg of the subject to be treated, preferably between 0.1 mg/kg and 20 mg/kg. Multiple doses can be used.

The composition of the present invention or its components can also be used in combination with other therapeutic agents for treating the same disease. Such combined use includes administration of these compounds and one or more other therapeutic agents at different times, or simultaneous use of these compounds and one or more other therapeutic agents. In some embodiments, the dosage of one or more compounds of the invention or other therapeutic agents used in combination can be modified, for example, by methods known to those of skill in the art to reduce the dose relative to the compound or therapeutic agent used alone.

It is to be understood that the combined use or combination includes use with other therapies, drugs, medical procedures, etc., wherein the other therapies or procedures may be administered at a time different from the composition of the present invention or its components (eg, in a short period of time (such as a few hours, such as 1, 2, 3, 4-24 hours) or in a longer period of time (such as 1-2 days, 2-4 days, 4-7 days, 1-4 weeks)) or at the same time as the composition of the invention or its components. The combined use also includes use with one-time or infrequently administered therapies or medical procedures (such as a surgery), accompanied by administration of the composition of the invention or its components within a short period of time or a longer period of time before or after the other therapies or procedures. In some embodiments, the present invention is used to deliver the composition of the present invention or its components and one or more other pharmaceutical therapeutic agents, and they are delivered by same or different routes.

The combined administration of any route of administration includes the delivery of the composition of the invention or its components and one or more other pharmaceutical therapeutic agents in any formulation by the same route of administration, including formulations in which the two compounds are chemically linked and retain their respective therapeutic activity when administered. In one aspect, the other drug therapy can be co-administered with the composition of the invention or its components. The combined use by co-administration includes the administration of the co-formulation or chemically linked compounds, or the administration in a short period of time (eg, within one hour, within 2 hours, within 3 hours, up to within 24 hours) of two or more compounds in independent formulations, which are administered by the same or different routes.

Co-administration of independent formulations includes co-administration by delivery via one device, such as the same inhalation device, the same syringe, etc., or administration by different devices within a short period of time relative to each other. A co-formulation of a compound of the present invention and one or more additional pharmacotherapies delivered by the same route of administration includes preparing the materials together so that they can be administered by one device, including combining different compounds in one formulation, or modifying compounds so that they are chemically linked together but still retain their biological activity. Such chemically linked compounds may include a linker that separates the two active ingredients, where the linker is substantially maintained in the body, or may be degraded in the body.

Method and Use

Another aspect of the present invention provides the use of the compound of formula I, or a deuterated compound or a pharmaceutically acceptable salt thereof in the manufacture of a medicament for the treatment of cerebral small vessel disease. Accordingly, the present invention provides the use of the compound of formula I, or a deuterated compound or a pharmaceutically acceptable salt thereof in the treatment of cerebral small vessel disease. Accordingly, the present invention provides a method for treating cerebral small vessel disease in a patient, the method comprising administering to the patient an effective amount of the compound of formula I, or a deuterated compound or a pharmaceutically acceptable salt thereof; or the above-mentioned pharmaceutical composition.

Another aspect of the present invention provides a method for enhancing the clearance of free hemoglobin outside the cerebral vessels in a patient, comprising administering to the patient an effective amount of a compound of formula I, or a deuterated compound or a pharmaceutically acceptable salt thereof; or the above-mentioned pharmaceutical composition. Another aspect of the present invention provides a method for clearing free hemoglobin outside the cerebral vessels in a patient, comprising administering to the patient an effective amount of a compound of formula I, or a deuterated compound or a pharmaceutically acceptable salt thereof; or the above-mentioned pharmaceutical composition.

In some embodiments, the cerebral small vessel disease is cerebral microbleed. In some embodiments, the cerebral microbleed in the patient is confirmed by MRI. In some embodiments, the patient is suffering from spontaneous cerebral microbleed, drug-related cerebral microbleed, or traumatic cerebral microbleed. In some embodiments, the spontaneous cerebral microbleed is age-related cerebral microbleed, hypertensive cerebral microbleed, cerebral microbleed associated with acute altitude sickness, cerebral microbleed associated with chronic altitude sickness, cerebral microbleed associated with ischemic stroke, or cerebral microbleed associated with hemorrhagic stroke. In some embodiments, the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed. In some embodiments, the traumatic cerebral microbleed is a cerebral microbleed caused by surgery.

EXAMPLES

Example 1. Triol Significantly Reduces the Expression of Inflammatory Cytokines Caused by the Activation of Microglia by Free Hemoglobin Methods Immunofluorescence Imaging of Tissue Sections:

The thickness of paraffin sections was 5 µm. For fresh paraffin sections, the sections were dried at 37° C. overnight and then dried at 55° C. for 30 minutes. The sections were quickly placed in xylene for dewaxing. After fully dewaxing with xylene for 10 min for 3 times, absolute ethanol-95% ethanol-90% ethanol-80% ethanol-70% ethanol-50% ethanol-ddH2O were successively used for gradient rehydration. After rehydration, the sections were placed in EDTA antigen repair solution for microwave high temperature repair. After the repair was completed, it was allowed naturally cool down to room temperature. Primary antibody incubation: the water around the tissue was absorbed with absorbent paper, the sample was circled out with an immunohistochemistry pen, the primary antibody diluted with DAKO antibody dilution was added, and incubated in a wet box at 4° C. overnight in the dark. After equilibrating at room temperature for 10 minutes, it was then washed with PBST for 3 times, each time for 5 minutes. Fluorescent secondary antibody of corresponding species was added, and then incubated in a wet box at room temperature in the dark for 1 h. After washing with PBST for 3 times, it was stained with Hochest33342 staining solution diluted with DAKO at room temperature in the dark for 10 minutes, followed by washing with PBST for 3 times, each time for 5 minutes. The sections were sealed with water-soluble agents, and then imaged using a laser confocal microscope. The method for confocal imaging was the same as that for cellular immunofluorescence. NIS-Elements Analysis software was used to analyze the fluorescence intensity of confocal images, which was then normalized with the fluorescence intensity per unit area according to the built-in scale.

Immunohistochemical Staining of Brain Tissue of Cynomolgus Monkeys:

The experiment was carried out according to routine immunohistochemical procedures, as follows: the thickness of paraffin sections of prefrontal cortex tissue of cynomolgus monkeys was 5 µm, and fresh paraffin sections were baked overnight at 37° C. Dewaxing: Paraffin sections were dried at 55° C. for 30 minutes, and then quickly placed in xylene for dewaxing, by placing in xylene for 10 min for 3 times for fully dewaxing. Rehydration: absolute ethanol-95% ethanol-90% ethanol-80% ethanol-70% ethanol-50% ethanol-ddH2O were successively used for immersion, each time 3 min, for gradient rehydration. After rehydration, the sections were placed in EDTA antigen repair solution for microwave high temperature repair for 30 min. After the repair was completed, it was allowed naturally cool to room temperature. Primary antibody incubation: the water around the tissue was absorbed with absorbent paper, the sample was circled out with an immunohistochemistry pen, the primary antibody diluted with DAKO antibody dilution was added, and incubated in a wet box at 4° C. overnight in the dark. After equilibrating at room temperature for 10 minutes, it was then washed with PBST for 3 times, each time for 5 minutes. HRP secondary antibody diluted in DAKO antibody diluent was added, and incubated at room temperature in a wet box for 1 h. It was then washed 3 times with PBST, followed by addition of DAB to develop the substrate, with the coloring time of each section being controlled to be the same. It was washed 1 time with PBST, followed by hematoxylin counterstaining for 10 s. The sections were rinsed gently with running water and then washed once with PBS. Dehydration: ddH2O-50% ethanol-70% ethanol-80% ethanol-90% ethanol-95% ethanol-absolute ethanol were successively used for immersion, each time 3 min, for gradient rehydration. Permeabilization: Permeabilization was performed with xylene for 10 min for 3 times. Sealing: Sealing was performed with neutral resin diluted with xylene. Two hours later the sealing agent was solidified and images could be taken. Imaging: Nikon ECLIPSE Ti-U inverted fluorescence microscope was used to take pictures of the sections in the bright field, by adjusting the appropriate exposure intensity and background white balance, and fixing the shooting adjustments to take pictures of each group of slices from multiple views and by multiples folds.

Western Blot:

1) Preparation of protein samples (see the instructions of M-PER protein lysate): After the cells had been processed for the specified time, the medium was aspirated and then washed with 4° C. pre-chilled PBS (0.01M pH7.2~7.3) for 3 times. 150-200 ul of M-PER protein lysate mixed with protease inhibitor (PMSF 100×) was added, which was lysed on ice for 10 minutes to fully lyse the cells. After collection of the lysate, the cell debris was removed by centrifugation at 4° C. and 12,000 rpm at low temperature for 15 minutes. 2) BCA protein quantification (see the instructions of BCA protein quantification kit): corresponding components were added to a 96-well detection plate by the ratio of quantification reagent A solution:B solution:ddH2O:protein=100:2:7.5:5, and albumin standards diluted in gradient concentration were added to draw a standard curve. Each sample was provided with 3 wells. After the sample was added, it was shaken gently and incubated in a 37° C. incubator for 30 minutes to complete the biuret reaction. After the reaction, the absorbance of each well at a wavelength of 562 nm was detected using a microplate reader. A standard curve of protein concentration was prepared using the average value of the standard OD, and a correlation coefficient $r2>0.99$ was regarded as good linearity. After calculating the protein concentration of each group of samples using the standard curve, protein lysate and 5× loading buffer were used to adjust the concentration of each sample to have the same concentration. By boiling in boiling water at 100° C. for 5 minutes, the protein was denatured into a primary structure. Centrifugation was performed at 12000 g for 5 s to remove the sample from the wall to the bottom. 3) Polyacrylamide gel electrophoresis: separated gel with appropriate concentration was prepared according to the molecular weight of the target protein to be measured, and concentrated gel was prepared after the separated gel was solidified, with a comb being inserted to avoid foaming. After the concentrated gel was completely solidified, color pre-stained marker and protein samples were loaded, and constant pressure electrophoresis was performed using the Bio-Rad electrophoresis system. The electrophoresis was stopped when the target protein indicated by the marker was separated. 4) Membrane transfer (wet transfer): PVDF membrane of appropriate size with glue was cut and pre-activated in methanol. After cutting the electrophoresis gel, it was sandwiched with PVDF membrane and sponge to form a four-layer sandwich to avoid air bubbles. The interlayer was placed in a electro-transfer membrane tank and pre-cooled wet transfer buffer was poured in, and 100V constant voltage condition was used for electro-transfer. The transfer time was adjusted according to the molecular weight of the target protein. 5) Blocking: the PVDF membrane was taken out after the membrane transfer was completed, which was washed in a TBST membrane washing solution for 3 times, 5 min/time. 5% skimmed milk powder was prepared with TBST, and the PVDF membrane was blocked in the 5% skimmed milk powder at room temperature for 1 hour. 6) Antibody incubation: After blocking, the membrane was washed for 3 times with 5% TBST washing solution, 5 min/time. The membrane was cut into several bands according to the molecular weight of the target protein, which were placed in the compartment box respectively. Corresponding primary antibodies were added, and incubated overnight in a shaker at 4° C. After primary antibody incubation was completed, the membrane was washed for 3 times with 5% TBST washing solution, 5 min/time. Secondary antibodies against corresponding primary antibody species were added, placed on a low-speed shaker, and incubated at room temperature for 1 h. 7) Exposure and development: The membrane was washed for 3 times with 5% TBST washing solution, 5 min/time. Developing solutions A and B were added to the cassette in a 1:1 ratio, and then mixed. After immersing the PVDF membrane in the developing solution for 1 min, it was exposed and developed using a Bio-Rad chemiluminescence system, and the images were analyzed using Image Lab software.

Statistical Processing:

The experimental results were expressed as mean±standard deviation, and statistical analysis was performed using SigmaPlot software. $P<0.05$ means the difference is statistically significant. Other special methods are shown in the note.

Results

Using a hypobaric chamber to simulate acute hypobaric hypoxia caused by the rapid approach to the plateau, we took the cynomolgus monkeys from 320 meters above sea level to 7500 meters in 190 minutes, and then treated the cynomolgus monkeys at the altitude of 7500 meters for 48 hours, simulating rapid reaching extremely high altitude under experimental conditions. As the altitude rose, cynomolgus monkeys displayed significant symptoms of acute altitude sickness, such as vomiting, ataxia, and confusion, indicating a successful replication of an acute altitude sickness model of non-human primate cynomolgus monkeys. The use of classic behavioral, pathological and biochemical tests showed that acute hypobaric hypoxia led to a significant decrease in the coordination of skeletal muscles, changes in vacuolation of brain tissue structure, rise in brain water content, cerebral vascular edema, and neuronal degeneration injury in cynomolgus monkeys, indicating that acute hypobaric hypoxia caused significant brain damage.

Figure 2:
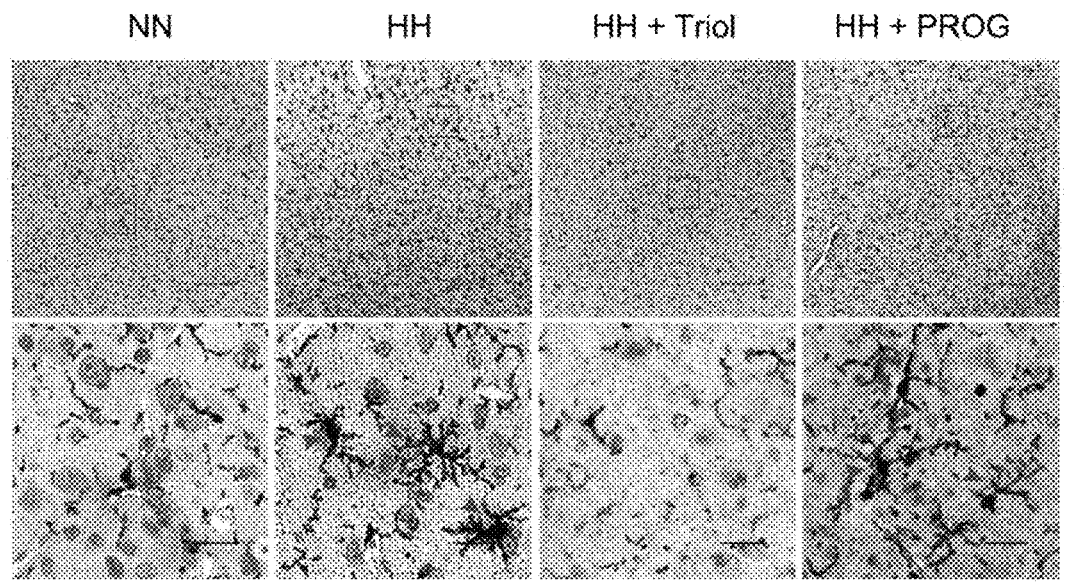
FIG. 2. Activation of microglia in the brain tissue of the prefrontal cortex of cynomolgus monkeys. A. Iba-1 immunohistochemical staining of the brain tissue of the prefrontal cortex of cynomolgus monkeys, Iba-1 serves as a marker for microglia activation. The black scale bar is 25 μm and the red scale bar is 200 μm. B. Statistics of Iba-1 relative optical density values. Image pro plus software was used to perform optical density scanning on the immunohistochemical images of each group to obtain the optical density values, which were then normalized with the NN group. NN: Normobaric Normoxia group (n=4); HH: Hypobaric Hypoxia group (n=4); HH+Triol: Hypobaric Hypoxia with Triol administration group (n=3); HH+PROG: Hypobaric Hypoxia with control drug administration group (n=4). One-way ANOVA analysis and Dunnutt's t test were used to perform statistical tests. ***, $p<0.01$, n.s., no statistical difference.
Figure 2:
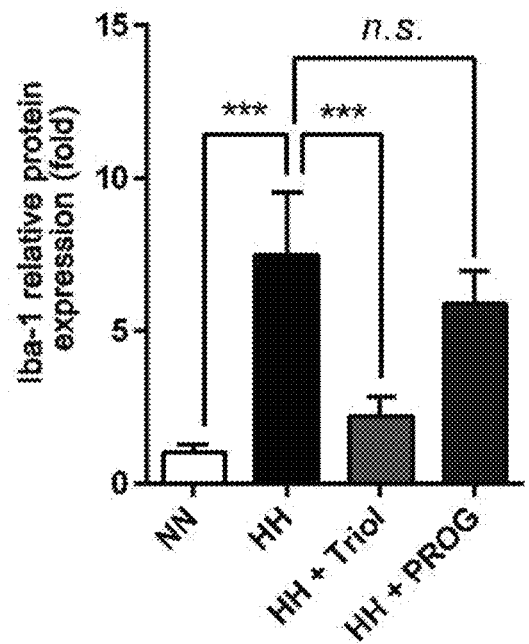
Figure 3:
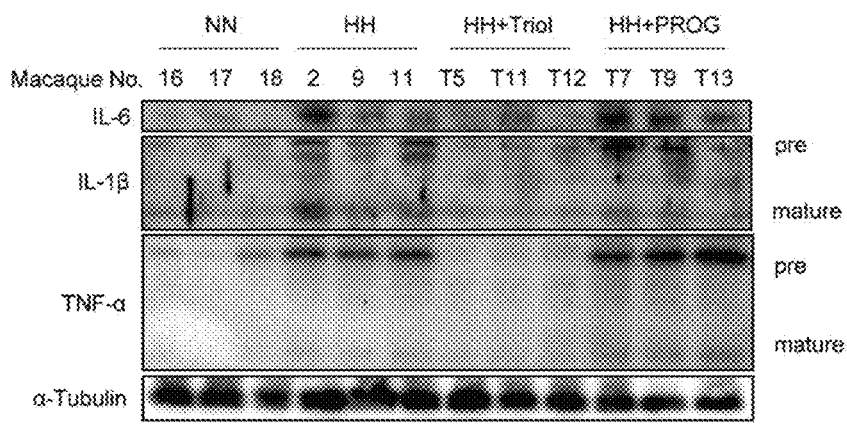
FIG. 3. Triol significantly reduced the expression of inflammatory factors IL-6, IL-1β and TNF-α in the brain tissue of cynomolgus monkeys. A. Protein expression of inflammatory factors IL-6, IL-1β and TNF-α in the brain tissue of the prefrontal cortex of cynomolgus monkeys; B. Statistics of protein relative gray scan values. NN: Normobaric Normoxia group (N=3); HH: Hypobaric Hypoxia group (N=3); HH+Triol: Hypobaric Hypoxia with Triol administration group (N=3); HH+PROG: Hypobaric Hypoxia with control drug administration group (N=3). The gray value was obtained by scanning with Image Lab software, and the relative value was obtained after normalizing with α-Tubulin. One-way ANOVA analysis and Dunnutt's t test were used to perform statistical tests, and in the latter each group was compared with the HH group, *, $p<0.05$; **, $p<0.01$.
Figure 3:
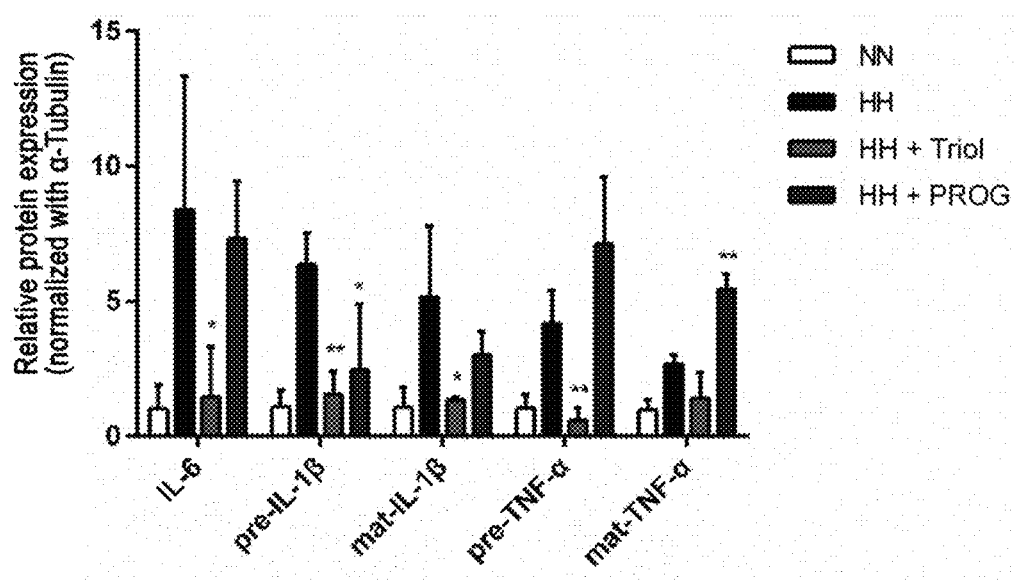

To investigate the possibility of hemoglobin to cause damage to the brain tissue of cynomolgus monkeys under acute hypobaric hypoxia, we performed immunofluorescence staining of the prefrontal cortex brain tissue of cynomolgus monkeys. The results are shown in FIG. 1. Compared with the normobaric normoxia group, the distribution of extravascular free hemoglobin was significantly increased in the acute hypobaric hypoxia group (FIG. 1A), while its distribution was significantly reduced in the Triol treatment group (FIG. 1B). Immunohistochemical staining of microglial activation marker Iba-1 (ionized calcium-binding adapter molecule 1) in the prefrontal cortex of cynomolgus monkeys showed that acute hypobaric hypoxia caused an increase in microglial filamentous or lamellar pseudopodia, showing an activation-like morphological change and an increase in Iba-1 expression (FIG. 2A), while the number of cells in the activation-like morphology decreased and the expression of Iba-1 decreased significantly in the Triol treatment group (FIG. 2B). In the brain tissue of the prefrontal cortex of the cynomolgus monkeys, Western blot was further used to analyze the effect of acute hypobaric hypoxia on the precursor and mature forms of inflammatory cytokines IL-6 (Interleukin 6), TNF-α (Tumor necrosis factor alpha) and IL-1β (Interleukin 1 beta). The results showed that acute hypobaric hypoxia treatment caused a significant increase in the expression of these inflammatory factors, while Triol significantly reduced the expression levels of these inflammatory cytokines (FIGS. 3A and 3B).

Example 2. Triol Significantly Restores the Hemoglobin Clearance in Brain Tissue CD163 is one of the molecular markers of M2 macrophages with anti-inflammatory activity. Its function is to participate in the intracellular clearance of hemoglobin molecules as the only hemoglobin scavenger receptor in mammals. The complex of hemoglobin and haptoglobin undergoes CD163-mediated phagocytosis on macrophages/microglia, and then is transported into the lysosome through the endosomes for degradation to produce heme, which is further degraded by HO-1 to produce $Fe^{2+}$, CO and biliverdin, and $Fe^{2+}$ and biliverdin will be further oxidized to $Fe^{3+}$ and bilirubin.

Figure 4:
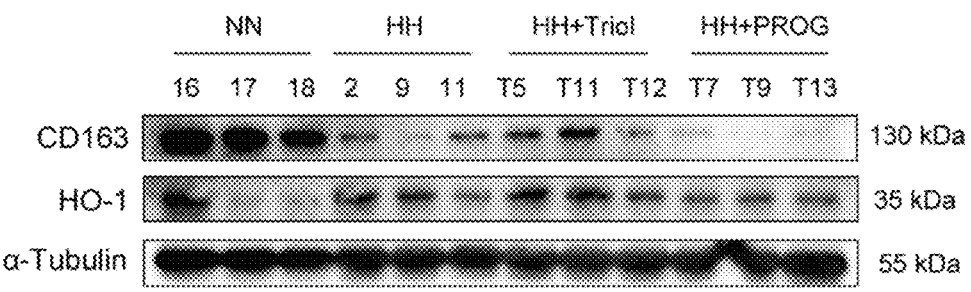
FIG. 4. Triol enhanced the clearance of free hemoglobin in brain tissue by up-regulating CD163 and Heme Oxygenase-1 (HO-1) protein levels. A. Protein expression of hemoglobin scavenger receptor CD163 and heme oxygenase HO-1 in the brain tissue of the prefrontal cortex of cynomolgus monkeys; B. Statistics of protein relative gray scan values. The gray value was obtained by scanning with Image Lab software, and the relative value was obtained after normalizing with α-Tubulin. NN: Normobaric Normoxia group (N=3); HH: Hypobaric Hypoxia group (N=3); HH+Triol: Hypobaric Hypoxia with Triol administration group (N=3); HH+PROG: Hypobaric Hypoxia with progesterone administration group (N=3). One-way ANOVA analysis and Dunnutt's t test were used to perform statistical tests, and in the latter each group was compared with the HH group, *, $p<0.05$; n.s., no statistical difference.
Figure 4:
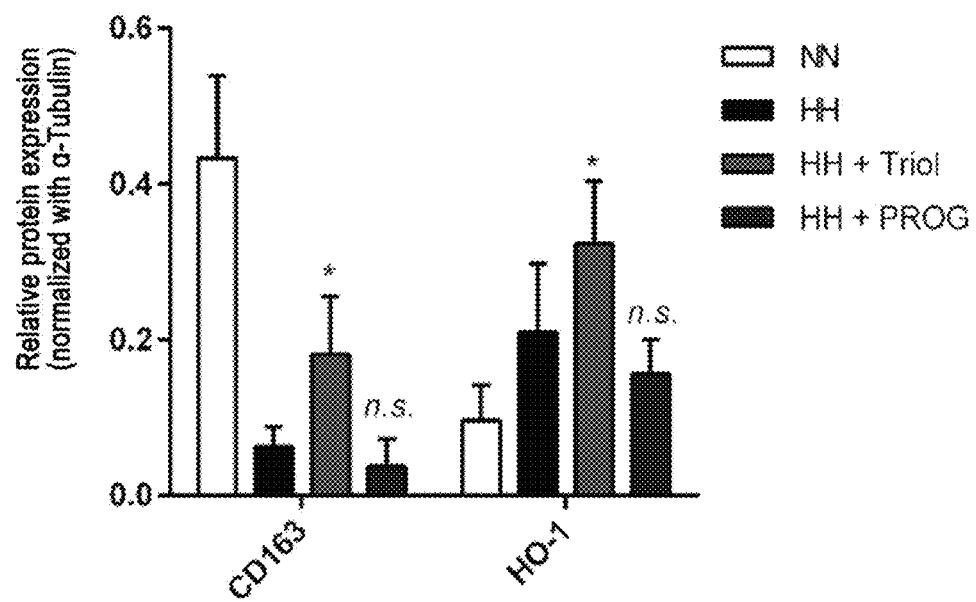

In order to analyze the effect of hypobaric hypoxia on hemoglobin clearance, we first examined the expression of CD163 and its downstream heme degradation key rate-limiting enzyme HO-1 in the prefrontal cortex brain tissue of cynomolgus monkeys. We found that acute hypobaric hypoxia caused a significant down-regulation of CD163 expression (FIGS. 4A and 4B), and this down-regulation of CD163 expression could be significantly restored by Triol. Consistent with reports in the literature, heme oxygenase HO-1 was stress-up-regulated after hypobaric hypoxia, and in this experiment Triol treatment further up-regulated the expression of HO-1.

Figure 5:
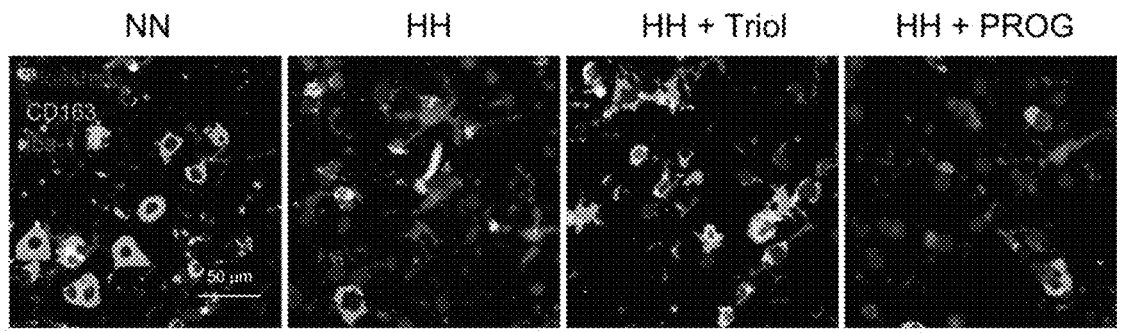
FIG. 5. Triol restored down-regulated CD163 and microglia activation caused by hypobaric hypoxia. A. Immunofluorescence imaging of CD163 and Iba-1 in the brain tissue of cynomolgus monkeys. B. Statistics of relative fluorescence intensity of CD163 and Iba-1. C. Correlation analysis of relative fluorescence intensity of CD163 and Iba-1. NN: Normobaric Normoxia group; HH: Hypobaric Hypoxia group; HH+Triol: Hypobaric Hypoxia with Triol administration group; HH+PROG: Hypobaric Hypoxia with progesterone administration group. One-way ANOVA analysis and Dunnutt's t test were used to perform statistical tests, and in the latter each group was compared with the HH group, ***, $p<0.001$.
Figure 5:
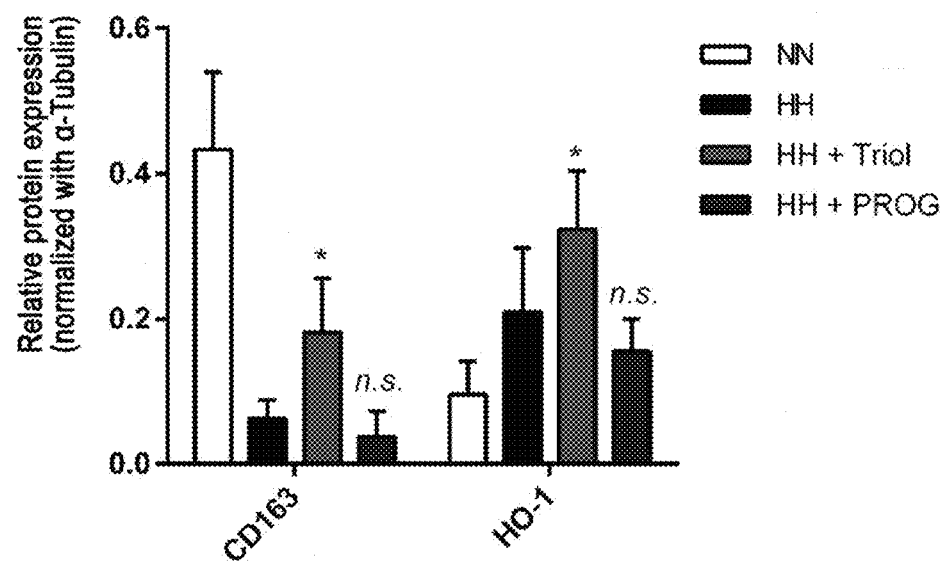
Figure 5:
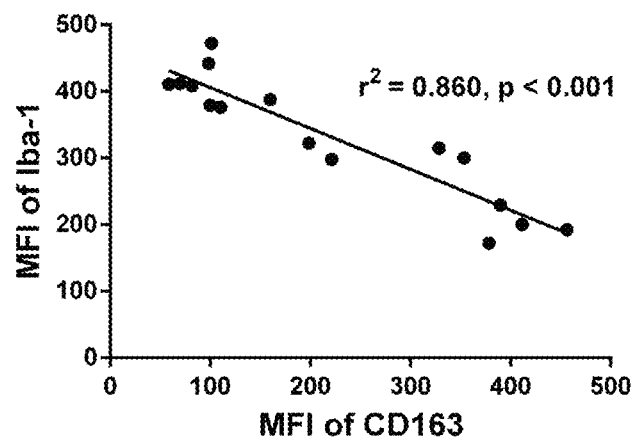

Immunofluorescence staining of the prefrontal cortex brain tissue of cynomolgus monkeys was used to further analyze the correlation between the change of CD163 expression and the microglia activation marker Iba1. Acute hypobaric hypoxia caused a significant down-regulation of CD163 expression (FIGS. 5A and 5B), accompanied by an increase in the expression of Iba1; and when this down-regulation of CD163 was significantly restored by Triol, it was accompanied by a down-regulation of Iba1 expression; and the control drug progesterone did not cancel the inhibition of CD163 expression caused by hypoxia, and the expression of Iba1 increased at this time.

The above results show that the expression patterns of CD163 and Iba1 are opposite, strongly suggesting that free hemoglobin is an inflammatory inducing factor of microglia in acute hypoxic hypoxic brain damage, and CD163-mediated hemoglobin clearance is severely inhibited by hypoxia.

Example 3. Triol Reduces the Inflammatory Activation of Microglia BV2 by Enhancing Hemoglobin Clearance Methods
Cell Culturing:
Microglial cells BV2 were recovered and cultured in a DMEM medium containing 10% FBS. When the cell density reached about 80%, sub-culturing and seeding were performed. The cell seeding density was about $4.0-5.0 \times 10^5$/mL.

Hypoxia Treatment:
After starting the cell program of a hypoxia workstation, the gas condition was set to 1% oxygen and 5% carbon dioxide. After 30 minutes of ultraviolet sterilization and when the gas concentration was stable, the test could be started. Before hypoxia treatment, the cells were replaced with fresh medium, and then the culture dish or confocal plate was placed in the hypoxia workstation. After a designated time point of treatment, the culture dish was quickly taken out, and cell fixation or protein lysis was performed.

Hemoglobin Treatment:
Free hemoglobin was prepared into 10 mM stock solution with sterile water, stored at 4° C., diluted with culture medium and added to the culture dish to reach the specified final concentration. During co-stimulating of 20 μM hemoglobin and hypoxia, the cells were stimulated with free hemoglobin first, and then the culture dish was immediately placed in a hypoxia workstation for hypoxia treatment.

Cellular Immunofluorescence Imaging:
The cells were seeded in a special dish for laser confocal imaging, replaced with fresh serum culture medium after attachment, and then fixed by applying corresponding hemoglobin stimulation, hypoxia treatment or co-treatment. First the medium was aspirated, washed for 3 times with 0.3% PBST, then added with 4% paraformaldehyde to fix the cells for 20 min. It was then washed for 3 times with 0.3% PBST, perforated with Triton X-100 for 15 min. Then it was washed for 3 times with 0.3% PBST, and corresponding primary antibody was diluted with DAKO antibody diluent and mixed, and then added onto the cells, followed by being placed in a closed wet box, and incubated overnight at 4 degrees shaker. After equilibrating at room temperature, it was washed with 0.3% PBST for 3 times. A specific concentration of fluorescent secondary antibody was diluted with DAKO antibody diluent and then added onto the sample, followed by being placed in a wet box in the dark and incubated at room temperature for 1 h. After washing with 0.3% PBST for 3 times, Hochest33342 nuclear staining solution was diluted with DAKO antibody diluent, and was added onto the sample after mixing, followed by being placed in a wet box in the dark and incubated at room temperature for 15 minutes. After the incubation, it was washed with PBS once, and 300 ul PBS was added, and pictures could be taken. Nikon A1 confocal microscope was used to take pictures. After the program was started, the laser intensity and exposure time of each channel were adjusted, and then the conditions of the imaging were fixed to take photos of each group of samples. Fluorescence intensity analysis of confocal images was performed using NIS-Elements Analysis software, and the fluorescence intensity per cell was normalized with the number of cells.

Western Blot:
Same as in Example 1.
Real-Time Quantitative Reverse Transcription PCR Amplification (qRT-PCR):
1) Extraction of total RNA: Trizol extraction reagent instructions were followed. After the cells were treated to a designated time point, the medium was aspirated and washed twice with PBS. 1 ml Triol was added to pipette lysed cells (the following reagents are calculated according to 1 ml Trizol). 200 ul of chloroform was added, mixed vigorously by hand, then placed at room temperature for 3 min. Centrifugation was performed at 12000 g at 4° C. for 15 minutes, and 400 ul of the upper water phase was taken into a new tube, 400 ul of isopropanol was added, gently mixed by hand, and placed at room temperature for 20 min. Centrifugation was performed at 12000 g at 4° C. for 10 minutes, and the supernatant was discarded. 500 ul of pre-chilled 75% ethanol was added, followed by centrifugation at 7500 g at 4° C. for 10 min, and the supernatant was carefully discarded. After air drying, appropriate amount of DEPC water was added to dissolve the RNA precipitate. 2) RNA quantification: Nanodrop 2000 nucleic acid quantifier was used to quantify the RNA, and the OD ratio at the wavelength of 260/280 nm was determined, and the ratio in the range of 1.8-2.0 was considered to be of good quality. 3) Reverse transcription reaction: the total amount of RNA in each reaction system was 2 ug, oligo dT 1 ul, and the reaction system was adjusted to 13 ul using DEPC water. After centrifugation and mixing, it was placed at 65° C. and pre-denatured for 5 min. Immediately after denaturation, it was put on ice, added with RT Reaction Buffer 4 ul, dNTP 2 ul, Reverse Transcriptase 1 ul. After centrifugation and mixing, reverse transcription reaction was performed. The reverse transcription reaction conditions were: 42° C. 60 min-70° C. 10 min-4° C. 4) qPCR amplification reaction parameters: qPCR amplification reaction system was: SYBR Green Mix 5 ul, cDNA 1 ul, primer 2 ul, RNase free ddH2O 2 ul. Cycle parameters were: Holding stage: 95° C. 15 min; Cycling stage (40 cycles): 95° C. 10 s-56° C. 20 s-72° C. 30 s; Melt Curve stage: 95° C. 15 s-60° C. 60 s-95° C. 15 s-60° C. 60 s. 5) Data processing: Applied Biosystem 7500 fast real-time PCR software v2.0.5 was used for data analysis, and the relative gene expression was quantified using the formula RQ=2−ΔΔCt method.

Results

Figure 6:
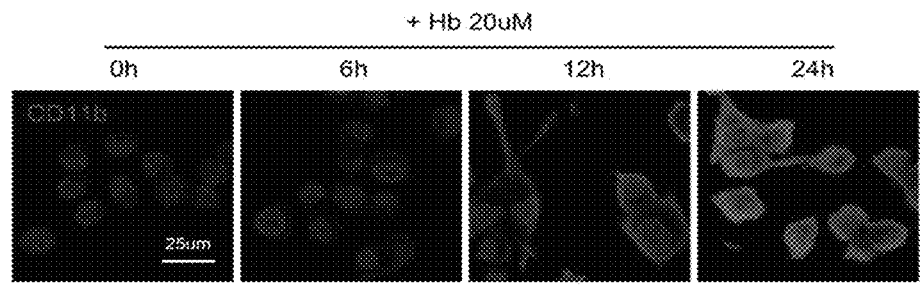
FIG. 6. Hypoxia exacerbated the inflammatory activation of microglia caused by free hemoglobin. A. After free hemoglobin stimulated microglia BV2 at different time points, immunofluorescence was performed to detect microglia activation marker CD11b. The scale bar is 25 μm. B. Statistics of the relative fluorescence intensity of CD11b in Fig. A. One-way ANOVA analysis and Dunnutt's t test were used to perform statistical tests, *, $p<0.05$; **, $p<0.01$. C. After free hemoglobin stimulated microglia BV2 at different time points. immunofluorescence was performed to detect microglial activation marker Iba-1, and phalloidin staining showed microglial morphological changes. D. Statistics of the relative fluorescence intensity of Iba-1 in Fig. C. One-way ANOVA analysis and Dunnutt's t test were used to perform statistical tests, *, $p<0.05$; **, $p<0.01$. E. At different time points using free hemoglobin to stimulate BV2, Western blot was used to detect the level of CD11b protein. F. After free hemoglobin stimulated microglia BV2 for 6 hours, qPCR was used to detect the mRNA expression of pro-inflammatory cytokines and chemokines. G. Hypoxia exacerbated the increase in protein expression of microglia inflammatory factors TNF-α, IL-1β and IL-6 caused by free hemoglobin, but had no effect on the anti-inflammatory factor IL-4.
Figure 6:
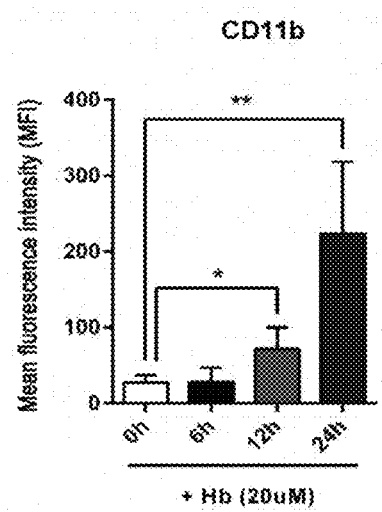
Figure 6:
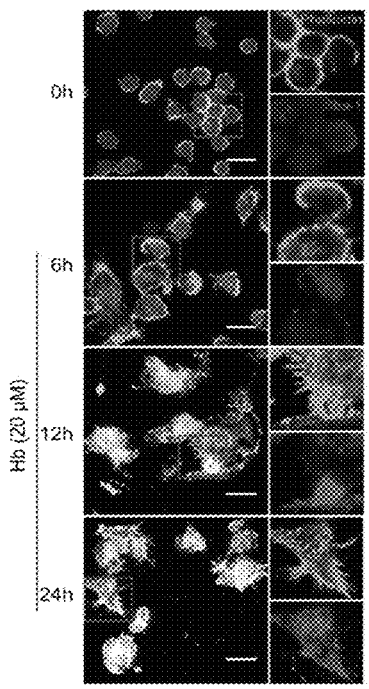
Figure 6:
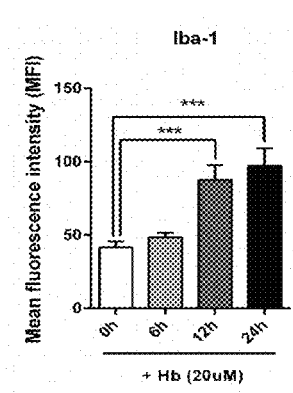
Figure 6:
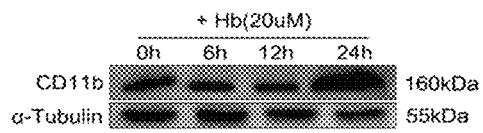

In order to explore whether free hemoglobin can directly cause the activation of microglia, hemoglobin was first used to stimulate microglia to observe the changes in their activation indexes. Using free hemoglobin to stimulate microglia BV2 in vitro at different times, the results showed that, at 24 hours, BV2 showed an activation-like morphology, presenting as an increase in cell body, and an increase and extension of filamentous pseudopodia (FIGS. 6A and 6C). At the same time, the expression of microglia activation molecular markers Iba-1 (FIG. 6D) and CD11b (FIGS. 6B and 6E) were also significantly increased by the stimulation of free hemoglobin (FIGS. 6B and 6D). Western blot experiments further confirmed the aforementioned immunofluorescence test results in the brain tissue of cynomolgus monkeys (FIG. 6E). Consistent with these observations, free hemoglobin stimulation caused a significant increase in the expression of microglia inflammatory cytokines TNF-α, IL-1β, and IL-6 mRNA levels (as shown in FIG. 6F), indicating that free hemoglobin caused inflammatory activation of microglia cells.

In order to analyze the effect of hypoxia on free hemoglobin-mediated activation of microglia, microglia was directly stimulated by free hemoglobin and at the same time, hypoxia treatment of 1% oxygen was applied to the cells. It was found that hypoxia exacerbated the increase in protein levels of microglia inflammatory cytokines caused by free hemoglobin. These inflammatory factors included TNF-α, IL-1β and IL-6, but had no significant effect on the anti-inflammatory cytokine IL-4 (FIG. 6G). These results show that hypoxia can exacerbate microglial activation caused by free hemoglobin.

Figure 7:
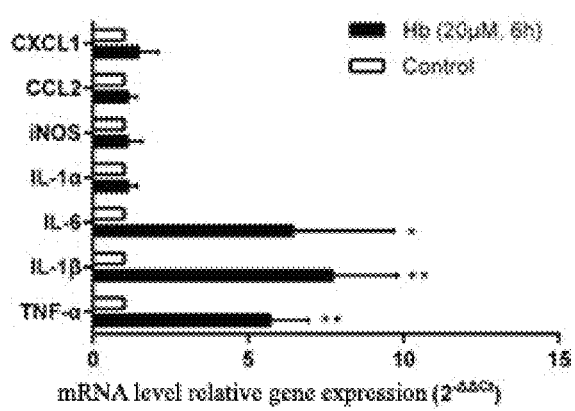
FIG. 7. After interfering the up-regulation of CD163 expression, the inhibitory effect of Triol on hypoxia and hemoglobin-induced upregulation of Iba-1 and CD11b was eliminated. According to the manufacturer's instructions, RNAiMAX was used to transfect CD163 No. 01 and scrambled interference fragment NC respectively to BV2 cells, BV2 cell culture medium was then added with or without 10 μM Triol, and BV2 cells were stimulated with 20 μM hemoglobin and 1% hypoxia for 6 hours, after which protein samples were collected, and the expression of microglial activation markers Iba-1 and CD11b was detected by Western blot.
Figure 7:
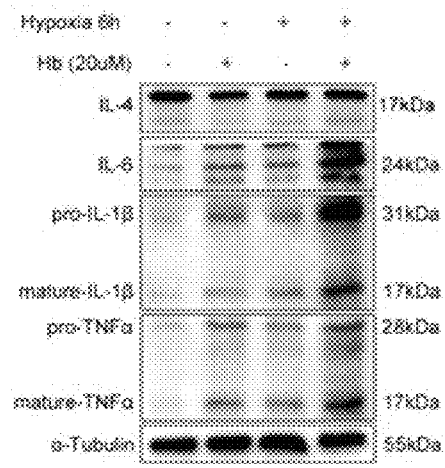
Figure 7:
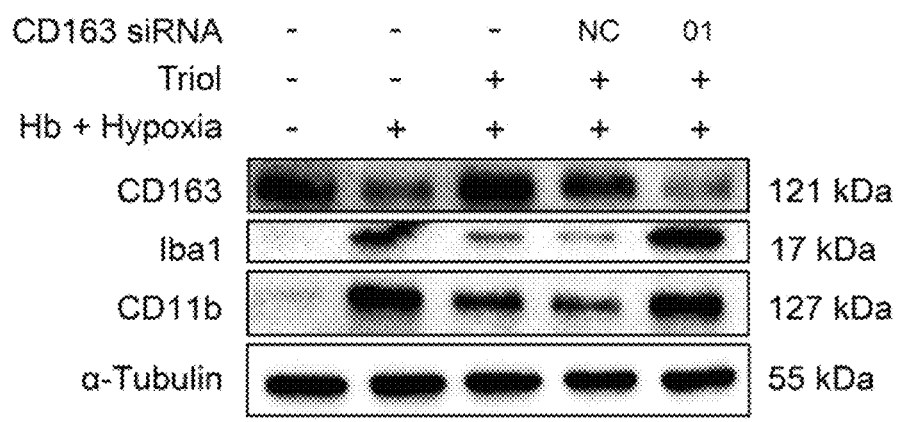

In the microglia of the brain tissue of cynomolgus monkeys, Triol was found to up-regulate the expressions of hemoglobin scavenging receptor CD163 and its downstream molecule HO-1. RNA interference of CD163 was further used in an in vitro cell model. After hypoxia and microglia activation with hemoglobin stimulation, it was analyzed whether the interference of CD163 could cancel the inhibitory effect of Triol on the activation of microglia. As shown in FIG. 7, after interfering CD163, the inhibitory effect of Triol on the up-regulation of Iba-1 and CD11b in hypoxia and hemoglobin-activated microglia cells was cancelled, and the expression of Iba-1 and CD11b resumed up-regulated, indicating that Triol prevents the inflammatory activation of microglia by enhancing CD163-mediated cell clearance of free hemoglobin.

In summary, free hemoglobin causes the activation of microglia, and Triol reduces the activation of microglia caused by free hemoglobin by restoring the expression of the scavenger receptor CD163.

REFERENCES

1. Expert Consensus Group for Diagnosis and Treatment of Cerebral Small Vessel Diseases. Expert Consensus for Diagnosis and Treatment of Cerebral Small Vessel Diseases, Chinese Clinicians, Vol. 42, No. 1, 2014: 84-87.
2. Zhu Yicheng. Important issues in clinical research of cerebral small vessel diseases, Chinese Journal of Stroke, December 2015, Vol. 10 No. 12: 996-999.
3. Wardlaw J M, Smith C, Dichgans M. Mechanisms of sporadic cerebral small vessel disease: insights from neuroimaging. Lancet Neurol, 2013, 12:483-497.
4. Li Feng, Tan Shouwen, Li Ying, Xu Chitian. Blood-brain barrier integrity and cerebral small vessel disease, International Journal of Cerebrovascular Diseases, 2017, 25(3): 239-243.
5. Zhang Zhijie, Yang Wanyong, Xu Anding. Cerebral microbleeds. Chinese Journal of Internal Medicine. 2015; 54(4):371-4.
6. Clarke, C. (2006). Acute mountain sickness: medical problems associated with acute and subacute exposure to hypobaric hypoxia. Postgraduate medical journal 82, 748-753.
7. Wilson, M. H., Newman, S., and Imray, C. H. (2009). The cerebral effects of ascent to high altitudes. The Lancet Neurology 8, 175-191.
8. Willmann, G., Fischer, M. D., Schatz, A., Schommer, K., and Gekeler, F. (2013). Retinal vessel leakage at high altitude. Jama 309, 2210-2212.
9. Yuan Qiang, Use value of MRI magnetic sensitivity weighted imaging in cerebral microbleeds in chronic high altitude disease, 2015, Master's thesis of Imaging Medicine and Nuclear Medicine of Qinghai University.
10. Greenberg S M, Vernooij M W, Cordonnier C, et al. Cerebral microbleeds: a guide to detection and interpretation. Lancet Neurol. 2009; 8:165-74.

The invention claimed is:

1. A method for treating a cerebral microbleed in a patient suffering from a cerebral microbleed, the method comprising administering to the patient an effective amount of a compound of formula I:

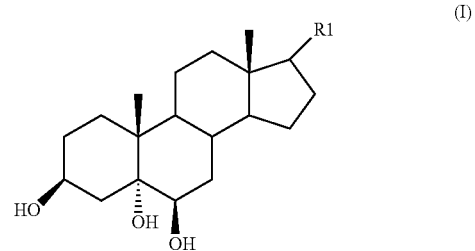

or a deuterated compound or a pharmaceutically acceptable salt thereof, wherein $R_1$ is H, an alkyl having 1 to 5 carbon atoms, or —CH(CH$_3$)(CH$_2$)$_3$CH(CH$_3$)$_2$, wherein the cerebral microbleed manifests as an increased distribution of free hemoglobin outside cerebral vessels; and wherein the cerebral microbleed is treated by clearing free hemoglobin outside the cerebral vessels in the patient.

2. The method of claim 1, wherein $R_1$ is H.

3. The method of claim 1, wherein $R_1$ is selected from a group consisting of —CH(CH$_3$)$_2$, and —CH(CH$_3$)(CH$_2$)$_3$CH(CH$_3$)$_2$.

4. The method of claim 1, wherein the cerebral microbleed is asymptomatic.

5. The method of claim 1, wherein the cerebral microbleed is symptomatic.

6. The method of claim 1, wherein the patient is a human.

7. The method of claim 1, wherein the method further comprises administering an additional therapeutic agent.

8. The method of claim 1, wherein the cerebral microbleed is spontaneous cerebral microbleed, drug-related cerebral microbleed, or traumatic cerebral microbleed.

9. The method of claim 8, wherein the spontaneous cerebral microbleed is age-related cerebral microbleed, hypertensive cerebral microbleed, cerebral microbleed associated with ischemic stroke, or cerebral microbleed associated with hemorrhagic stroke.

10. The method of claim 8, wherein the drug-related cerebral microbleed is thrombolytic drug-related cerebral microbleed, anticoagulant drug-related cerebral microbleed, antiplatelet aggregation drug-related cerebral microbleed, or statin drug-related cerebral microbleed.

11. The method of claim 8, wherein the traumatic cerebral microbleed is a cerebral microbleed caused by a surgery.

12. The method of claim 11, wherein the surgery is a surgery that directly involves the central nervous system.

13. The method of claim 11, wherein the surgery is cerebral aneurysm clipping or embolization, or brain tumor resection.

14. A method for treating cerebral microbleeds in a patient exhibiting reduced expression of CD163, the method comprising administering to the patient an effective amount of a compound of formula I:

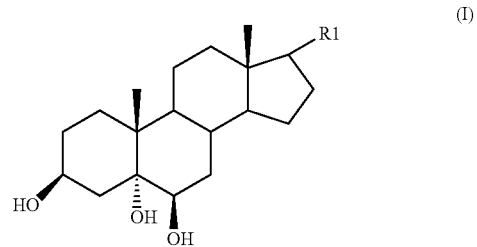

or a deuterated compound or a pharmaceutically acceptable salt thereof, wherein $R_1$ is H, an alkyl having 1 to 5 carbon atoms, or —CH(CH$_3$)(CH$_2$)$_3$CH(CH$_3$)$_2$, wherein the cerebral microbleed manifests as an increased distribution of free hemoglobin outside cerebral vessels; and wherein the cerebral microbleed is treated by clearing free hemoglobin outside the cerebral vessels in the patient.

* * * * *